(12) United States Patent
Cornelius et al.

(10) Patent No.: US 12,186,394 B2
(45) Date of Patent: *Jan. 7, 2025

(54) COMPOSITIONS AND METHODS FOR TREATMENT OF PRE-CANCEROUS SKIN LESIONS

(71) Applicant: Washington University, St. Louis, MO (US)

(72) Inventors: Lynn Cornelius, St. Louis, MO (US); Shadmehr Demehri, St. Louis, MO (US); Raphael Kopan, St. Louis, MO (US)

(73) Assignee: Washington University, St. Louis, MO (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/946,905

(22) Filed: Sep. 16, 2022

(65) Prior Publication Data

US 2023/0026855 A1 Jan. 26, 2023

Related U.S. Application Data

(63) Continuation of application No. 17/140,782, filed on Jan. 4, 2021, now Pat. No. 11,478,549, which is a continuation of application No. 15/510,443, filed as application No. PCT/US2015/049434 on Sep. 10, 2015, now Pat. No. 10,905,763.

(60) Provisional application No. 62/048,586, filed on Sep. 10, 2014.

(51) Int. Cl.
| | |
|---|---|
| *C07D 243/04* | (2006.01) |
| *A61K 31/513* | (2006.01) |
| *A61K 31/59* | (2006.01) |
| *A61K 31/593* | (2006.01) |
| *A61K 45/06* | (2006.01) |

(52) U.S. Cl.
CPC ............ *A61K 45/06* (2013.01); *A61K 31/513* (2013.01); *A61K 31/59* (2013.01); *A61K 31/593* (2013.01); *C07D 243/04* (2013.01); *A61K 2300/00* (2013.01)

(58) Field of Classification Search
CPC .... C07D 243/04; A61K 45/06; A61K 31/513; A61K 31/59
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,755,388 A | 7/1988 | Heath et al. | |
| 4,820,711 A | 4/1989 | Pearlman | |
| 4,828,837 A | 5/1989 | Uster et al. | |
| 4,925,661 A | 5/1990 | Huang | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 5,264,618 A | 11/1993 | Felgner et al. | |
| 6,242,435 B1 | 6/2001 | Achkar | |
| 6,566,495 B1 | 5/2003 | Fodor et al. | |
| 7,939,313 B2 | 5/2011 | Heyduk et al. | |
| 8,299,109 B2 | 10/2012 | Nordsiek et al. | |
| 10,905,763 B2 | 2/2021 | Cornelius et al. | |
| 2005/0079235 A1 | 4/2005 | Stockfleth | |
| 2005/0214328 A1 | 9/2005 | Zeldis | |
| 2009/0098065 A1 | 4/2009 | Harel | |
| 2017/0246299 A1 | 8/2017 | Cornelius et al. | |

FOREIGN PATENT DOCUMENTS

| | | |
|---|---|---|
| EP | 1491188 A1 | 12/2004 |
| WO | 0000159 A2 | 1/2000 |
| WO | 2006120682 A2 | 11/2006 |
| WO | 2010080345 A1 | 7/2010 |
| WO | 2012074842 A2 | 6/2012 |
| WO | 2012076212 A2 | 6/2012 |
| WO | 2012176212 A1 | 12/2012 |
| WO | 2016040638 A2 | 3/2016 |

OTHER PUBLICATIONS

Clinicaltrials.gov, "History of Changes for Study: NCT02019355 Actinic Keratosis Study (AK)," Clinical Trials Study NCT02019355, Dec. 17, 2013.
Examination Report for New Zealand Patent Application No. 730890, dated Sep. 7, 2023, 4 pages.
Abel E.L., et al., "Multi-Stage Chemical Carcinogenesis in Mouse Skin: Fundamentals and Applications," Nature Protocols, 2009, vol. 4, No. 9 pp. 1350-1362.
Berth-Jones J., et al., "Vitamin D Analogues and Psoriasis," British Journal of Dermatology, Blackwell Publishing Ltd, Aug. 1992, vol. 127, No. 2, pp. 71-78.
Bucknall M., et al., "Practical Quantitative Biomedical Applications of MALDI-TOF Mass Spectrometry," Journal of the American Society for Mass Spectrometry, Elsevier Science Inc, 2002, vol. 13, pp. 1015-1027.

(Continued)

*Primary Examiner* — Sikarl A Witherspoon
(74) *Attorney, Agent, or Firm* — Polsinelli PC

(57) ABSTRACT

The present disclosure encompasses compositions and methods for the treatment of precancerous skin lesions. Compositions of the invention comprise a cytotoxic agent and a thymic stromal lymphopoietin (TSLP) inducer.

19 Claims, 9 Drawing Sheets

(9 of 9 Drawing Sheet(s) Filed in Color)

(56) References Cited

OTHER PUBLICATIONS

Communication Pursuant to Article 94(3) EPC in European Patent Application No. 15840602.5, mailed Aug. 17, 2020, 4 Pages.
Cornelius L., "Actinic Keratosis Study (AK)," U.S. National Library of Medicine, NCT02019355, ClinicalTrials.gov, Dec. 24, 2013, 7 Pages, Retrieved from URL: https://clinicaltrials.gov/ct2/show/NCT02019355.
Davis S.A., et al., "Top Dermatologic Conditions in Patients of Color: An Analysis of Nationally Representative Data," Journal of Drugs Dermatology, Apr. 2012, vol. 11, No. 4, pp. 466-473.
Demehri S., et al., "Elevated Epidermal Thymic Stromal Lymphopoietin Levels Establish an Antitumor Environment in the Skin," Cancer Cell, Oct. 16, 2012, vol. 22, No. 4, pp. 494-505, DOI: 10.1016/j.ccr.2012.08.017, XP028948539.
Devaux S., et al., "Topical Vitamin D Analogues Alone or in Association with Topical Steroids for Psoriasis: A Systematic Review," Journal of the European Academy of Dermatology and Venereology, May 2012, vol. 26, Suppl. 3, pp. 52-60.
Di Piazza M., et al., "Loss of Cutaneous TSLP-Dependent Immune Responses Skews the Balance of Inflammation from Tumor Protective to Tumor Promoting," Cancer Cell, Oct. 16, 2012, vol. 22, No. 4, pp. 479-493, DOI:10.1016/i.ccr.2012.08.016, XP028948537.
"Dovonex Cream 0.005% Drug Description," RxList, The Internet Drug Index, Sep. 23, 2005, pp. 1-2, [Retrieved on Nov. 9, 2015] Retrived from URL: http://www.rxlist.com/dovonex-ointment-drug.htm.
Extended European Search Report for European Application No. 15840602.5, mailed Apr. 17, 2018, 9 Pages.
Extended European Search Report for European Application No. 21193984.8, mailed Dec. 22, 2021, 11 Pages.
Fenske N.A., et al., "Actinic Keratoses: Past, Present and Future," Journal of Drugs in Dermatology, May 2010, vol. 9. No. 5 (Supplement) ODAC Conf. Pt. 1, pp. s45-s49.
Final Office Action for U.S. Appl. No. 15/510,443, mailed Dec. 2, 2019, 15 Pages.
Final Office Action for U.S. Appl. No. 15/510,443, mailed Jun. 15, 2018, 12 Pages.
Fullerton A., et al., "Guidelines for Measurement of Skin Colour And Erythema. A Report From the Standardization Group of the European Society of Contact Dermatitis," Contact Dermatitis, 1996, vol. 35, No. 1, pp. 1-10, DOI: 10.1111/j.1600-0536.1996.tb02258.x, XP055138222.
Giacomel J., et al., "Pink Lesions," Dermatologic Clinics, Elsevier Inc, Oct. 2013, vol. 31, No. 4, pp. 649-678.
International Preliminary Report on Patentability for International Application No. PCT/US2015/049434, mailed Mar. 23, 2017, 7 Pages.
International Search Report and Written Opinion for International Application No. PCT/US2015/049434, mailed Dec. 11, 2015, 8 Pages.
Kim R.H., et al., "Nonmelanoma Skin Cancer," Dermatologic Clinics, Elsevier Inc, Jan. 2012, vol. 30, No. 1, pp. 125-139.
Ebwohl M., et al., "Ingenol Mebutate Gel for Actinic Keratosis," New England Journal of Medicine, Mar. 15, 2012, vol. 366, No. 11, pp. 1010-1019, DOI:10.1056/NEJMoa1111170, XP002693228.
Li M., et al., "Topical Vitamin D3 and Low-Calcemic Analogs Induce Thymic Stromal Lymphopoietin in Mouse Keratinocytes and Trigger an Atopic Dermatitis," Proceedings of the National Academy of Sciences of the United States of America, Aug. 1, 2006, vol. 103, No. 31, p. 11736-11741, DOI:10.1073/pnas.0604575103, XP002410505.
Ma Y., et al., "Vitamin D in Combination Cancer Treatment," Journal of Cancer, 2010, vol. 1, pp. 101-107.
Majewski S., et al., "Combination of Isotretinoin And Calcitriol for Precancerous And Cancerous Skin Lesions," Lancet, Nov. 26, 1994, vol. 344, No. 8935, pp. 1510-1511.
Milczarek M., et al., "Vitamin D Analogs Enhance the Anticancer Activity of 5-fluorouracil in an In Vivo Mouse Colon Cancer Model," BMC Cancer, Jun. 18, 2013, vol. 13, No. 294, 19 pages.

Non Final Office Action for U.S. Appl. No. 15/510,443, mailed May 2, 2019, 15 Pages.
Non-Final Office Action for U.S. Appl. No. 15/510,443, mailed Oct. 6, 2019, 10 Pages.
Notice of Allowance for European Patent Application No. 15840602.5, mailed Mar. 26, 2021, 7 Pages.
Notice of Allowance for Ukrainian Application No. 201703381, mailed Dec. 16, 2019, 9 pages.
Notice of Allowance for U.S. Appl. No. 15/510,443, mailed Sep. 30, 2020, 08 Pages.
Office Action for Australian Patent Application No. 2015315047, mailed Dec. 2, 2019, 04 Pages.
Office Action for Australian Patent Application No. 2020281015, mailed Oct. 7, 2021, 5 Pages.
Office Action for Brazilian Application No. BR122021004073-7, mailed on Aug. 26, 2022, 3 pages.
Office Action for Brazilian Application No. BR122021004073-7, mailed on Dec. 21, 2022, 3 pages.
Office Action for Brazilian Patent Application No. BR112017004893-0, mailed Dec. 8, 2022, 05 Pages.
Office Action for Canadian Patent Application No. 2,963,922, mailed Nov. 16, 2021, 7 Pages.
Office Action for Chinese Patent Application No. 201580060643.8, mailed Mar. 8, 2019, 12 Pages.
Office Action for Eurasian Patent Application No. 201790565 mailed Dec. 16, 2019, 6 pages, with English Translation.
Office Action for European Patent Application No. 15840602.5, mailed Aug. 13, 2019, 5 Pages.
Office Action for Mexican Application No. MX/A/2017/003262, mailed Apr. 9, 2021, 7 Pages.
Office Action for Ukrainian Patent Application No. 201703381, mailed Mar. 26, 2019, 11 Pages.
Pommergaard H-C., et al., "Topical Combination Of Diclofenac, Calcipotriol, And Difluoromethylornithine Has Beneficial Effects Comparable to 5-fluorouracil For the Treatment of Non-melanoma Skin Cancer in Mice," Journal of Chemotherapy, Apr. 2014, vol. 26, No. 2, pp. 105-110, DOI:10.1179/1973947813Y.0000000117, ISSN 1973-9478, XP009510816.
Psorcutan Cream 0.005%, Universal Drugstore, 2 Pages, [Retrieved on Sep. 22, 2017] Retrieved from URL: https://www.universaldrugstore.com/medications/Dovonex+Cream/0.005%25.
Rockett J.C., et al., "DNA Arrays: Technology, Options and Toxicological Applications," Xenobiotica, 2000, vol. 30, No. 2, pp. 155-177.
Sato-Deguchi E., et al., "Topical Vitamin D3 Analogues Induce Thymic Stromal Lymphopoietin and Cathelicidin in Psoriatic Skin Lesions," British Journal of Dermatology, Jul. 2012, vol. 167, No. 1, pp. 77-84.
Seckin D., et al., "Can Topical Calcipotriol be a Treatment Alternative in Actinic Keratoses? A Preliminary Report," Journal of Drugs in Dermatology, May 2009, vol. 8, No. 5, pp. 451-454, XP055417714.
Smit J.V., et al., "Actinic Keratoses in Renal Transplant Recipients Do Not Improve with Calcipotriol Cream and All-Trans Retinoic Acid Cream As Monotherapies or in Combination During A 6-week Treatment Period," British Journal of Dermatology, Blackwell Publishing Ltd., Oct. 2002, vol. 147, No. 4, pp. 816-818.
Soumelis V., et al., "Human Epithelial Cells Trigger Dendritic Cell-Mediated Allergic Inflammation by Producing TSLP," Nature Immunology, Jul. 2002, vol. 3, No. 7, pp. 673-680.
Takahashi H., et al., "Photodynamic Therapy Using a Novel Photosensitizer, TONS501, is Similarly Effective to ALA and EC036 Photodynamic Therapy on DMBA-and TPA-Induced Mouse Skin Papilloma," Journal of Dermatological Science, Jun. 2012, vol. 66, pp. 221-224.
Tanghetti E.A., "The Role of Topical Vitamin D Modulators in Psoriasis Therapy," Journal of Drugs Dermatology, Aug. 2009, vol. 8, No. 8 (Supplement), pp. s4-s8.
Van Den Bemd G.J.C.M., et al., "Vitamin D and Vitamin D Analogs in Cancer Treatment," Current Drug Targets, Feb. 1, 2002, vol. 3, No. 1, pp. 85-94.

(56) References Cited

OTHER PUBLICATIONS

Warino L., et al., "Frequency and Cost of Actinic Keratosis Treatment," Dermatologic Surgery, Blackwell Publishing Inc., Aug. 2006, vol. 32, No. 8, pp. 1045-1049.

Ziegler S.F., et al., "Sensing the Outside World: TSLP Regulates Barrier Immunity," Nature Immunology, Apr. 2010, vol. 11, No. 4, pp. 289-293, DOI: 10.1038/ni. 1852, XP055453580.

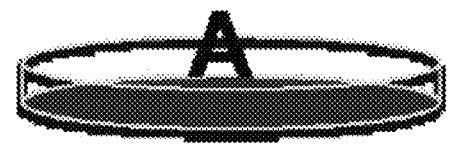 vs. 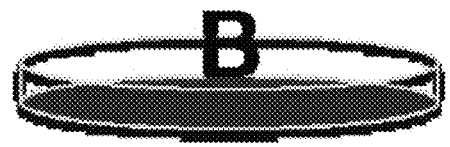
FIG. 6A  FIG. 6B

COMPOSITIONS AND METHODS FOR TREATMENT OF PRE-CANCEROUS SKIN LESIONS

CROSS REFERENCE TO RELATED APPLICATIONS

This application claims the benefit of U.S. application Ser. No. 17/140,782, filed Jan. 4, 2021, which is a continuation of U.S. application Ser. No. 15/510,443, filed Mar. 10, 2017, now U.S. Pat. No. 10,905,763, which claims the benefit of International patent application number PCT/US2015/049434, Filed Sep. 10, 2015, which claims priority of U.S. provisional application No. 62/048,586, filed Sep. 10, 2014, the disclosures of which are hereby incorporated by reference in their entirety.

GOVERNMENTAL RIGHTS

This invention was made with government support under GM054479 awarded by the National Institutes of Health. The government has certain rights in the invention.

FIELD OF THE INVENTION

The present disclosure encompasses compositions and methods for the treatment of precancerous skin lesions. Compositions of the invention comprise a cytotoxic agent and a thymic stromal lymphopoietin (TSLP) inducer.

BACKGROUND OF THE INVENTION

Non-melanoma skin cancers represent the most common type of cancer affecting a large number of individuals in the United States [1]. These cancers can lead to significant morbidity including ulceration, infection and local disfigurement if left untreated. Importantly, in the case of squamous cell carcinoma, precursor lesions that can be identified clinically as actinic keratoses can be treated early in order to prevent them from developing to full-blown cutaneous malignancies necessitating costly surgical procedures. In addition to destructive treatments used for clinically visible actinic keratoses (e.g. cryotherapy), several topical treatments have been developed, which can also treat the subclinical lesions. These field-directed treatments include photodynamic therapy, 5-fluorouracil and imiquimod [2]. However, the effectiveness of the current treatments, the treatment duration and the severity of the side effects associated with these treatments have limited the patients' compliance and their therapeutic efficacy. Therefore, there is a need to develop new treatments for actinic keratosis that can deliver optimal outcome with fewer applications and side effects. Considering that the annual cost of care for actinic keratosis alone in the United States is over $900 million [3], an effective treatment that can eliminate actinic keratosis and prevent skin cancer development will also have a major impact on our healthcare system.

SUMMARY OF THE INVENTION

In an aspect, the present invention encompasses a method to treat a precancerous skin lesion. The method comprises topically administering to the lesion a composition comprising a cytotoxic agent and a thymic stromal lymphopoietin (TSLP) inducer.

In another aspect, the present invention encompasses a method to prevent the transition of a precancerous skin lesion to skin cancer. The method comprises: (a) identifying a subject with one or more precancerous skin lesion(s); and (b) topically administering to the precancerous skin lesion(s) a composition comprising a cytotoxic agent and a TSLP inducer, wherein the precancerous skin lesion(s) is reduced in size such that progression to skin cancer is prevented.

In still another aspect, the present invention encompasses a method to prevent a precancerous skin lesion from occurring. The method comprises topically administering to a subject at risk of developing a precancerous skin lesion a composition comprising a cytotoxic agent and a TSLP inducer.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 5A) Scalp, (FIG. 5B) Face, (FIG. 5C) RUE and (FIG. 5D) LUE. Note that due to short duration of the treatment, no participant experienced erythema scores of 3 or 4, which are commonly seen in patients treated with 5-FU twice daily for 2-3 weeks (standard of care regimen).

FIG. 6A and FIG. 6B depict the two treatment regimens used for the images presented in FIG. 6C.

DETAILED DESCRIPTION OF THE INVENTION

Figure 1A:
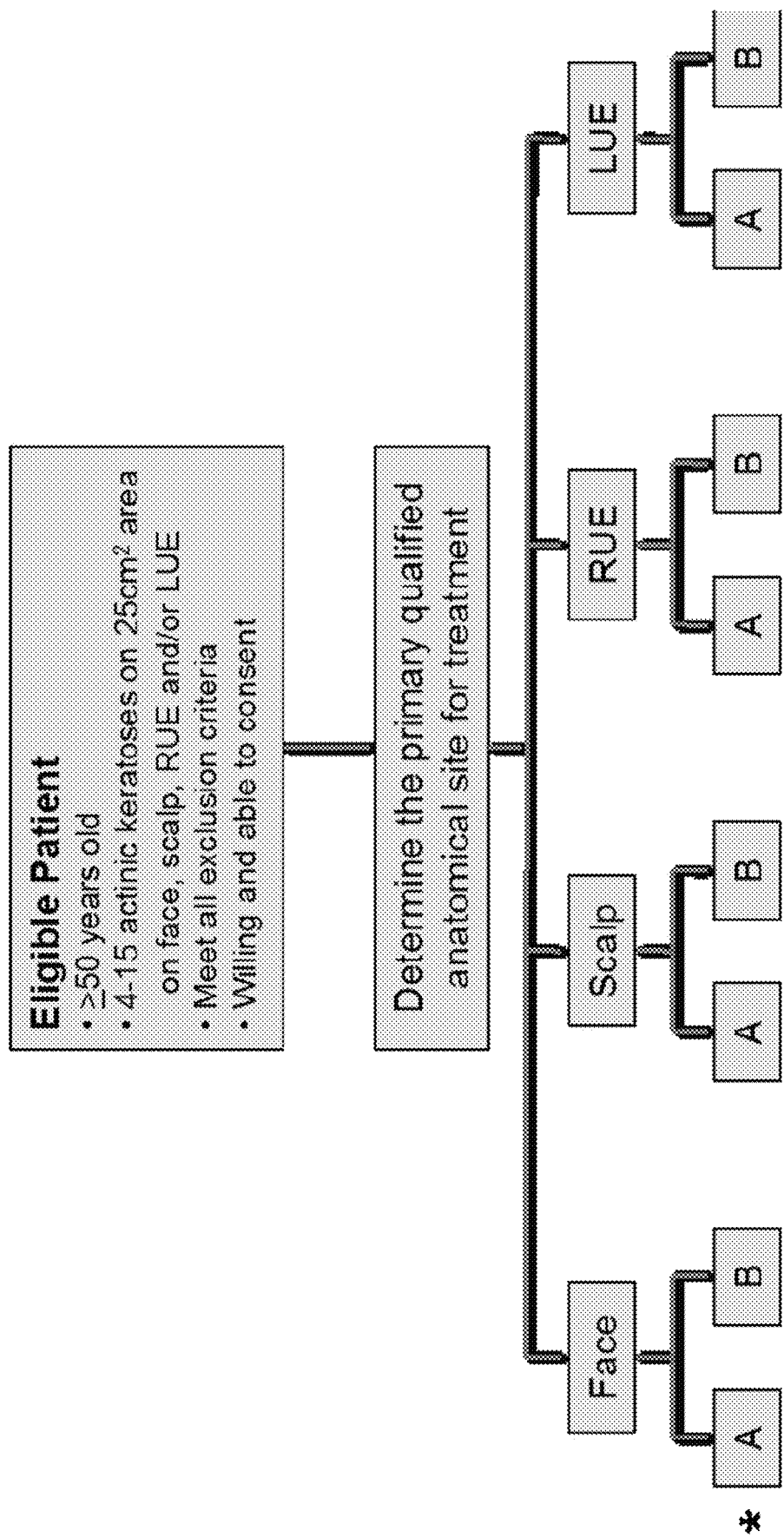
FIG. 1A depicts a schematic of the randomization of patients. Eligible patients are enrolled and all of their qualified anatomical sites for treatment are evaluated and photographed. Medication randomization will be based on the participant's primary qualified anatomical site that is picked by the treating physician. After the medication assignment is determined, participants will apply the same medication to all of their qualified anatomical sites. *: Study medication will be dispensed according to randomization list for each primary anatomical site, but participants will apply the same medication to all of their qualified anatomical sites. RUE: right upper extremity; LUE: left upper extremity.

Applicants have surprisingly discovered that a topical composition comprising a cytotoxic agent and a thymic stromal lymphopoietin (TSLP) inducer significantly reduces the number and size of precancerous skin lesions. The reduction in lesion number and size occurs with a shortened course of treatment thereby reducing the risk of adverse effects. Accordingly, the present disclosure provides compositions and methods for preventing and treating various skin lesions. Additional aspects of the invention are described below.

I. Compositions

In an aspect, a composition of the invention comprises a cytotoxic agent and a thymic stromal lymphopoietin (TSLP) inducer. In a specific embodiment, a composition of the invention comprises 5-fluorouracil (5-FU) and a vitamin D analog. A vitamin D analog may be modified to improve bioavailability, solubility, stability, handling properties, or a combination thereof, as compared to an unmodified version. Thus, in another aspect, a composition of the invention comprises modified vitamin D. In still another aspect, a composition of the invention comprises a prodrug of a vitamin D analog.

A composition of the invention may optionally comprise one or more additional drugs or therapeutically active agent in addition to the cytotoxic agent and TSLP inducer. A composition of the invention may further comprise a pharmaceutically acceptable excipient, carrier or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants.

Other aspects of the invention are described in further detail below.

(a) Cytotoxic Agent

As used herein, a "cytotoxic agent" is an agent that affects rapidly dividing cells in general. A cytotoxic agent is any naturally-occurring, modified, or synthetic compound that is toxic to rapidly dividing cells. Such agents are useful in the treatment of neoplasms, and in the treatment of other symptoms or diseases characterized by cell proliferation or a hyperactive cell population. The cytotoxic agent may be an alkylating agent, an antimetabolite, an anti-tumor antibiotic, an anti-cytoskeletal agent, a topoisomerase inhibitor, an anti-hormonal agent, a targeted therapeutic agent, an angiogenesis inhibitor, a growth inhibitory polypeptide, a photodynamic therapeutic agent, an antineoplastic agent, or a combination thereof. In a specific embodiment, the cytotoxic agent may be selected from the group consisting of an antimetabolite and a photodynamic therapeutic agent.

Non-limiting examples of suitable alkylating agents may include altretamine, benzodopa, busulfan, carboplatin, carboquone, carmustine (BCNU), chlorambucil, chlornaphazine, cholophosphamide, chlorozotocin, cisplatin, cyclosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Non-limiting examples of suitable anti-tumor antibiotics may include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents may include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors may include, but are not limited to, amsacrine, etoposide (VP-16), irinotecan, mitoxantrone, RFS 2000, teniposide, and topotecan.

Non-limiting examples of suitable anti-hormonal agents may include aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents may include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib.

Non limiting examples of angiogeneisis inhibitors may include angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide.

Non limiting examples of growth inhibitory polypeptides may include bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1 BB ligand, and Apo-1 ligand.

Other antineoplastic agents may include anagrelide, arsenic trioxide, asparaginase, bexarotene, bropirimine, celecoxib, chemically linked Fab, efaproxiral, etoglucid, ferruginol, Ionidamide, masoprocol, miltefosine, mitoguazone, talapanel, trabectedin, and vorinostat.

In certain embodiments, the cytotoxic agent is a photodynamic therapeutic agent. Non-limiting examples of photodynamic therapeutic agents may include aminolevulinic acid, methyl aminolevulinate, retinoids (alitretinon, tamibarotene, tretinoin), and temoporfin. In a specific embodiment, the photodynamic therapeutic agent is aminolevulinic acid.

In a specific embodiment, the cytotoxic agent is an antimetabolite. Suitable antimetabolites may include, but are not limited to, aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcitabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate. In a specific embodiment, the antimetabolite is 5-fluorouracil (5-FU). 5-FU is a drug that is a pyrimidine analog which is used in the treatment of cancer. It is a suicide inhibitor and works through irreversible inhibition of thymidylate synthase.

Generally, the dosage form of the cytotoxic agent is either a cream or topical solution. However, other suitable dosage forms of the cytotoxic for topical administration are contemplated. Pharmaceutical compositions adapted for topical administration may be formulated as ointments, creams, suspensions, lotions, powders, solutions, pastes, gels, sprays, aerosols, oils, or salves. Topical administration may also involve the use of transdermal administration such as transdermal patches or iontophoresis devices. In a specific embodiment, the pharmaceutical composition is applied as a topical ointment or cream.

Dosages of cytotoxic agent can vary depending upon the disease or disorder to be treated and/or the age and condition of the subject to be treated. In an embodiment where the composition comprising a cytotoxic agent and a TSLP inducer is administered to a subject, the concentration of cytotoxic agent in the composition may be from about 0.01% to about 25%, or about 0.1% to about 10% or, more preferably, from about 0.5% to about 5%. For example, the concentration of cytotoxic agent in the composition may be about 0.1%, about 0.2%, about 0.3%, about 0.4%, about 0.5%, about 0.6%, about 0.7%, about 0.8%, about 0.9%, about 1%, about 1.5% about 2%, about 2.5%, about 3%, about 3.5% about 4%, about 4.5%, about 5%, about 5.5%, about 6%, about 6.5%, about 7%, about 7.5%, about 8%, about 8.5%, about 9%, about 9.5%, or about 10%. Alternatively, the concentration of cytotoxic agent in the composition may be about 10%, about 11%, about 12%, about 13%, about 14%, about 15%, about 16%, about 17%, about 18%, about 19%, about 20%, about 21%, about 22%, about 23%, about 24% or about 25%. In certain embodiments, the concentration of cytotoxic agent in the composition may be about 0.5%, about 1%, about 2%, about 2.5% or about 5%. In another embodiment, the concentration of cytotoxic agent in the composition is about 2% to about 5%. In a specific embodiment, the concentration of cytotoxic agent in the composition is about 2.5%. In still another embodiment, the concentration of cytotoxic agent in the composition is about 5%.

In certain embodiments, the cytotoxic agent is aminolevulinic acid. Dosages of aminolevulinic acid can vary depending upon the disease or disorder to be treated, the age and condition of the subject to be treated. In an embodiment where the composition comprising aminolevulinic acid and TSLP inducer is administered to a subject, the concentration of aminolevulinic acid in the composition may be from about 10% to about 25% or, more preferably, from about 15% to about 20%. For example, the concentration of aminolevulinic acid in the composition may be about 10%, about 11%, about 12%, about 13%, about 14%, about 15%, about 16%, about 17%, about 18%, about 19%, about 20%, about 21%, about 22%, about 23%, about 24% or about 25%. In certain embodiments, the concentration of aminolevulinic acid in the composition may be about 18% to about 22%. In an embodiment, the concentration of aminolevulinic acid in the composition is about 8% to about 12%. In a specific embodiment, the concentration of aminolevulinic acid in the composition is about 10%. In another embodiment, the concentration of aminolevulinic acid in the composition is about 20%.

In a specific embodiment, the cytotoxic agent is 5-FU. Dosages of 5-FU can vary depending upon the disease or disorder to be treated, the age and condition of the subject to be treated. In an embodiment where the composition comprising 5-FU and TSLP inducer is administered to a subject, the concentration of 5-FU in the composition may be from about 0.1% to about 10% or, more preferably, from about 0.5% to about 5%. For example, the concentration of 5-FU in the composition may be about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%. In certain embodiments, the concentration of 5-FU in the composition may be about 0.5%, about 1%, about 2%, about 2.5% or about 5%. In an embodiment, the concentration of 5-FU in the composition is about 2% to about 5%. In a specific embodiment, the concentration of 5-FU in the composition is about 2.5%. In another embodiment, the concentration of 5-FU in the composition is about 5%.

(b) Thymic Stromal Lymphopoietin (TSLP) Inducer

As used herein, a "TSLP inducer" is any compound that is capable of inducing thymic stromal lymphopoietin (TSLP). TSLP is an epithelial-derived cytokine that belongs to the interleukin-7 (IL-7) cytokine family. The inventors have found that TSLP acts as a potent anti-tumor cytokine in the skin by recruiting CD4+ Th2 cells to mount an immune surveillance in the skin. Methods to determine if a compound induces TSLP are known in the art. For example, TSLP nucleic acid expression, TSLP protein expression, or TSLP activity may be measured as described in more detail below in Sections I(b)i,ii,iii. Non-limiting examples of TSLP inducers include vitamin D analogs, polyinosinic-polycytidylic acid (poly(I:C) and other TLR3 ligands), FSL-1 (and other TLR2-TLR6 ligand), flagellin (and other TLR5 ligand), beta2-adrenoceptor agonists, cAMP-elevating agents (e.g., Forskolin), fatty acids (heptanoic acid, octanoic acid, nonanoic acid, and decanoic acid), xylene, 1,2,4-trimethylbenzene, 12-O-tetradecanoylphorbol-13-acetate (TPA, tetradecanoylphorbol acetate, tetradecanoyl phorbol acetate, and phorbol 12-myristate 13-acetate (PMA)), dibutyl phthalate (DBP), and diisononyl phthalate (DINP).

In a specific embodiment, a TSLP inducer may be vitamin D or an analog thereof. Vitamin D refers to a group of fat-soluble secosteroids. Secosteroids are very similar in structure to steroids except that two of the B-ring carbon atoms of the typical four steroid rings are not joined, whereas in steroids they are. Active vitamin D, or calcitriol, is a compound of formula (I):

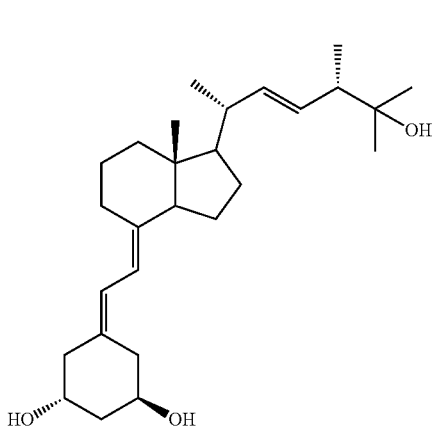

Formula (I)

Vitamin $D_3$, also known as cholecalciferol, is a form of vitamin D and is generated in the skin of animals when light energy is absorbed by a precursor molecule 7-dehydrocholesterol. Vitamin $D_3$, or cholecalciferol, is a compound of formula (II):

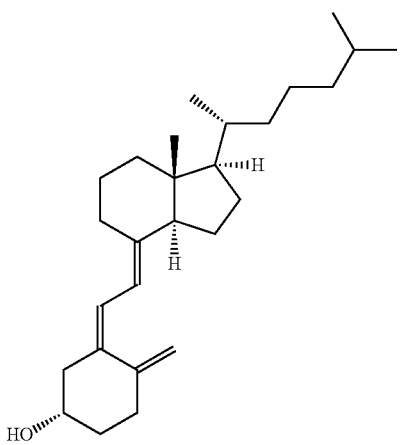

Formula (II)

Structurally modified derivatives of vitamin D may be referred to as vitamin D analogs. Vitamin D analogs may be modified to improve bioavailability, solubility, have improved stability and/or handling properties compared to an unmodified version. Prodrugs of vitamin D analogs are also contemplated. Any vitamin D analog capable of binding to vitamin D receptor and inducing thymic stromal lymphopoietin (TSLP) may be suitable for a composition of the invention. Vitamin D analogs are many, and will be recognized by the skilled person, Non-limiting examples of suitable vitamin D analogs include $1,25\text{-}(OH)_2D_3$ (calcitrol), $26,27\text{-}F_6\text{-}1,25\text{-}(OH)_2D_3$ (ST-630), $1\alpha\text{-}(OH)D_2$, $1\alpha\text{-}(OH)D_3$, $1,24\text{-}(OH)_2D_3$ (TV-02), 22-oxacalcitriol (OCT), calcipotriol (MC 903), $1,25\text{-}(OH)_2\text{-}16\text{-ene-}23\text{-yne-}D_3$ (Ro 23-7553). EB 1089, ED-71, PRI-2191, PRI-2205, cholecalciferol, ergocalciferol, calciferol, Calcijex, calcitriol, doxercalciferol, Hectorol, paricalcitol, Rocaltrol, Daivonex, and Zemplar. The term "analog", in the context of the present invention, is meant to include synthetic analogs as well as vitamin D metabolitesin a specific embodiment, the vitamin D analog is calcipotriol. Calcipotriol, or calcipotriene, or calcitrene, or Dovonex®, is a compound of formula (III):

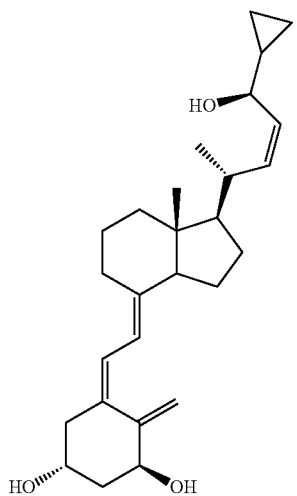

Formula (III)

Generally, the dosage form of a TSLP inducer is a cream, ointment or topical solution. However, other suitable dosage forms of a TSLP inducer for topical administration are contemplated. Pharmaceutical compositions adapted for topical administration may be formulated as ointments, creams, suspensions, lotions, powders, solutions, pastes, gels, sprays, aerosols, oils, or salves. Topical administration may also involve the use of transdermal administration such as transdermal patches or iontophoresis devices. In some embodiments, the pharmaceutical composition is applied as a topical ointment or cream.

Dosages of the TSLP inducer can vary depending upon the disease or disorder to be treated and/or the age and condition of the subject to be treated. In an embodiment where the composition comprising a cytotoxic agent and a TSLP inducer is administered to a subject, the concentration of TSLP inducer in the composition may be from about 0.001% to about 20%, from about 0.001% to about 10%, from about 0.001% to about 1%, from about 0.001% to about 0.1% or, more preferably, from about 0.001% to about 0.01%. For example, the concentration of TSLP inducer in the composition may be about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, or about 1.0%. In an exemplary embodiment, the concentration of TSLP inducer in the composition is about 0.002% to about 0.005%. In another exemplary embodiment, the concentration of TSLP inducer in the composition is about 0.0025%. In still another exemplary embodiment, the concentration of TSLP inducer in the composition is about 0.005%.

In a specific embodiment, the TSLP inducer is a vitamin D analog. Dosages of the vitamin D analog can vary depending upon the disease or disorder to be treated and/or the age and condition of the subject to be treated. In an embodiment where the composition comprising 5-FU and a vitamin D analog is administered to a subject, the concentration of vitamin D analog in the composition may be from about 0.001% to about 0.1% or, more preferably, from about 0.001% to about 0.01%. For example, the concentration of vitamin D analog in the composition may be about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%. In an exemplary embodiment, the concentration of vitamin D analog in the composition is about 0.002% to about 0.005%. In another exemplary embodiment, the concentration of vitamin D analog in the composition is about 0.0025%. In still another exemplary embodiment, the concentration of vitamin D analog in the composition is about 0.005%.

i. TSLP Nucleic Acid Expression

In an embodiment, TSLP nucleic acid expression may be measured to identify a compound that induces TSLP. For example, when TSLP nucleic acid expression is increased in the presence of a compound relative to an untreated control, the compound induces TSLP. In a specific embodiment, TSLP mRNA may be measured to identify a compound that induces TSLP.

Methods for assessing an amount of nucleic acid expression in cells are well known in the art, and all suitable methods for assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array. The term "hybridize" or "hybridizable" refers to sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression may be determined using PCR. Methods of PCR are well and widely known in the art, and may include quantitative PCR, semi-quantitative PCR, multiplex PCR, or any combination thereof. Specifically, the amount of nucleic acid expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire mRNA transcript for a nucleic acid sequence, or measuring a portion of the mRNA transcript for a nucleic acid sequence. For instance, if a nucleic acid array is utilized to measure the amount of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. Such a control nucleic acid should not specifically hybridize with an mRNA nucleotide sequence of the invention. This allows comparisons between assays that are performed on different occasions.

ii. TSLP Protein Expression

In another embodiment, TSLP protein expression may be measured to identify a compound that induces TSLP. For example, when TSLP protein expression is increased in the presence of a compound relative to an untreated control, the compound induces TSLP. In a specific embodiment, TSLP protein expression may be measured using immunoblot. In another specific embodiment, TSLP protein expression may be measured using immunofluorescence staining.

Methods for assessing an amount of protein expression are well known in the art, and all suitable methods for assessing an amount of protein expression known to one of skill in the art are contemplated within the scope of the invention. Non-limiting examples of suitable methods to assess an amount of protein expression may include epitope binding agent-based methods and mass spectrometry based methods.

In some embodiments, the method to assess an amount of protein expression is mass spectrometry. By exploiting the intrinsic properties of mass and charge, mass spectrometry (MS) can resolve and confidently identify a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can use mass spectrometry to look for the level of protein encoded from a target nucleic acid of the invention.

In some embodiments, the method to assess an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In general, an epitope binding agent-based method of assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, Ni2+, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In some embodiments, the epitope binding agent-based method is an ELISA. In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC) or immunofluorescence. IHC uses an antibody (or fluorescently labeled antibody in the case of immunofluorescence) to detect and quantify antigens in intact tissue samples. The tissue samples may be fresh-frozen and/or formalin-fixed, paraffin-embedded (or plastic-embedded) tissue blocks prepared for study by IHC or immunofluorescence. Methods of preparing tissue block for study by IHC or immunofluorescence, as well as methods of performing IHC or immunofluorescence are well known in the art.

iii. TSLP Activity

In an embodiment, TSLP activity may be measured to identify a compound that induces TSLP. TSLP is an epithelial-derived cytokine that belongs to the interleukin-7 (IL-7) cytokine family. TSLP acts as a potent anti-tumor cytokine in the skin by recruiting CD4+Th2 cells. Accordingly, inflammation and/or Th2 cells may be measured as an indication of TSLP activity. Inflammation may be measured using methods standard in the art. For example, inflammation may be measured visually using IHC, immunofluorescence and/or RT-PCR. Non-limiting markers of inflammation that may be examined include GR1, CD3, CD4, CD8, CD11b, CD11c, CD117, B220 and IFNγ. When inflammation is increased in the presence of a compound relative to an untreated control, the compound induces TSLP.

In another embodiment, CD4+ cells and/or CD8+ cells may be measured as an indication of TSLP activity. The amount of CD4+ cells and/or CD8+ cells may be measured using methods standard in the art. For example, CD4+ cells and/or CD8+ cells may be measured using flow cytometry. When the amount of CD4+ and/or CD8+ cells are increased in the presence of a compound relative to an untreated control, the compound induces TSLP.

(c) Components of the Composition

The present disclosure also provides pharmaceutical compositions. The pharmaceutical composition comprises a cytotoxic agent and a TSLP inducer, as active ingredients, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered topically by a number of different means that will deliver a therapeutically effective amount of the active ingredients. Such compositions administered topically in dosage unit formulations may contain conventional nontoxic pharmaceutically acceptable carriers, adjuvants, and vehicles as desired. Topical administration may also involve the use of transdermal administration such as transdermal patches or iontophoresis devices. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a cytotoxic agent and a TSLP inducer is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a cytotoxic agent and a TSLP inducer in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a cytotoxic agent and a TSLP inducer may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which sphingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetonitrile, alcohols, dimethylformamide, tetrahydrofuran, or combinations thereof.

Liposomes carrying a cytotoxic agent and a TSLP inducer may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase.

The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The cytotoxic agent and a TSLP inducer may be encapsulated in a microemulsion by any method generally known in the art.

In yet another embodiment, a cytotoxic agent and a TSLP inducer may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

The inventors have unexpectedly discovered that a composition comprising a cytotoxic agent and a TSLP inducer is significantly more effective than a cytotoxic agent alone in treating precancerous skin lesions with a shorter course of treatment. This unexpected discovery has the added benefit of decreasing adverse events thereby potentially improving patient compliance. The TSLP inducer serves to induce expression of TSLP thereby modulating the immune environment in the skin. The cytotoxic agent induces apoptosis in cells which releases antigens that augment the immune response mounted by the TSLP inducer.

In an aspect, the disclosure encompasses a method to treat a precancerous skin lesion, the method comprising topically administering to the lesion a composition comprising a cytotoxic agent and a TSLP inducer. In a specific embodiment, the composition may be administered for up to 7 days.

In another embodiment, the disclosure encompasses a method to prevent a precancerous skin lesion from occurring, the method comprising topically administering to a subject at risk of developing a precancerous skin lesion a composition comprising a cytotoxic agent and a TSLP inducer. In a specific embodiment, the composition may be administered for up to 7 days. As used herein, "a precancerous skin lesion" is a skin lesion that has the potential to progress to skin cancer, but is not cancer. Non-limiting examples of types of precancerous lesions may include actinic keratosis (solar keratosis), actinic cheilitis (Farmer's lip), cutaneous horn, mole (nevus), and dysplastic nevi. In a specific embodiment, the precancerous skin lesion is actinic keratosis. Methods of identifying precancerous skin lesions are known in the art. For example, a skin biopsy or dermascopy may identify a precancerous skin lesion. A review of dermascopy and its use in the diagnosis of precancerous skin lesions is provided in Giacomel et al., Dermatol Clin 2013, 31:649-678, which is hereby incorporated by reference in its entirety. For example, on dermoscopy, facial nonpigmented actinic keratoses (AKs) typically reveal whitish-yellow surface scale and a strawberry pattern, the latter consisting of an erythematous (pink to red colored) pseudonetwork surrounding hair follicles. The hair follicle openings are surrounded by a white halo and filled with a yellowish keratotic plug, forming a peculiar targetoid appearance. In addition, fine, linear-wavy vessels are often seen surrounding the hair follicles. Furthermore, small coiled vessels are occasionally visible in AK on the face. Histology may also be used to diagnose a precancerous lesion. For example, actinic keratoses (AKs) are defined at the histologic level by dysplasia and consist of keratinocytes manifesting atypical nuclei that are enlarged, irregular, and hyperchromatic. AKs also display disorganized growth, which disrupts differentiation and results in a thickened stratum corneum with retained nuclei. To stratify degrees of epidermal dysplasia, a three-tiered grading scale has been proposed for AKs that parallels that used for evaluation of cervical dysplasia. The histological features of keratinocytic intraepidermal neoplasia I (KIN I) are cellular atypia of basal keratinocytes confined to the lower third of the epidermis. KIN II shows atypical keratinocytes occupying the lower two-thirds of the epidermis, and KIN III shows atypical keratinocytes throughout the epidermis; this latter stage is equivalent to carcinoma in situ. The localized epidermal atypia in AKs reflects a partial disruption of the differentiation program, whereas a more complete disruption of the differentiation program is associated with SCC in situ (SCCIS). The KIN grading criteria evaluates the macroscopic and microscopic features of AKs. Further, clinical presentation, patient history, such as UV exposure, and appearance of the lesion may identify a precancerous lesion. For example, actinic keratosis (AK) typically appears on sun-exposed areas such as the face, bald scalp, lips, and the back of the hands. An actinic keratosis lesion may be flat to slightly raised, usually less than 1 inch in diameter, rough in texture, dry, scaly, and resembles warts. Most become red, but some will be tan, pink, red, and/or flesh-toned. In a specific embodiment, methods of the invention may be used to treat KIN I, KIN II, and/or KIN III type AK lesions.

In another aspect, the disclosure also encompasses a method to prevent the transition of a precancerous lesion to skin cancer, the method comprising identifying a subject with one or more precancerous skin lesion(s) and topically administering to the precancerous skin lesion(s) a composition comprising a cytotoxic agent and a TSLP inducer, wherein the precancerous skin lesion(s) is reduced in size such that progression to skin cancer is prevented. In a specific embodiment, the composition may be administered for up to 7 days. In another specific embodiment, the skin cancer is non-melanoma skin cancer. Untreated actinic keratoses can advance to squamous cell carcinoma (SCC). Accordingly, the disclosure encompasses a method to prevent the transition of an actinic keratosis lesion to squamous cell carcinoma, the method comprising identifying a subject with one or more actinic keratosis lesion(s) and topically administering to the actinic keratosis lesion(s) a composition comprising a cytotoxic agent and a TSLP inducer, wherein the actinic keratosis lesion(s) is reduced in size such that progression to squamous cell carcinoma is prevented. In a specific embodiment, the composition may be administered for up to 7 days.

In another aspect, the invention encompasses a method of treating a noncancerous skin lesion. The method comprises identifying a subject with one or more noncancerous skin lesion (s) and topically administering to the noncancerous skin lesion (s) a composition comprising a cytotoxic agent and a TSLP inducer, wherein the noncancerous skin lesion (s) is reduced in size. In a specific embodiment, the composition may be administered for up to 10 days. Suitable noncancerous skin lesions may include warts and similar virus infections of the skin. Non-limiting examples of warts may include plantar warts, cutaneous warts, anogenital warts, verruca vulgaris, flat warts, filiform warts and wart-like lesions associated with virus infections of the skin such as human papillomaviruses and Molluscum Contagiosum. Methods to diagnose warts are known in the art. Generally, a skilled artisan may be able to diagnose a wart via an examination. However, a biopsy may also be used to diagnose a wart. Warts may appear anywhere on the body, however the face, hand, finger, foot, leg and genitalia are most common. Warts may appear rough, smooth, flat, raised, contain black "seeds", round, oval, and lighter or darker than surrounding skin.

In still another aspect, the invention encompasses a method of treating non-melanoma skin cancer. The method comprises identifying a subject with non-melanoma skin cancer and topically administering to the non-melanoma skin cancer a composition comprising a cytotoxic agent and a TSLP inducer, wherein the non-melanoma skin cancer is reduced in size. In a specific embodiment, the composition may be administered for up to 10 days. Non-limiting examples of types of non-melanoma skin cancer may include basal cell carcinoma, squamous cell carcinoma, Bowen disease, keratoacanthomas, Merkel cell carcinoma, cutaneous (skin) lymphomas, Kaposi sarcoma, skin adnexal tumors, sebaceous gland carcinoma, and sarcomas. About 80% of skin cancer develops from basal cells and is called basal cell carcinoma. Basal cell carcinoma most often develops on the head and neck. It is mainly caused by sun exposure or develops in people who received radiation therapy as children. This type of skin cancer usually grows slowly and rarely metastasizes (spreads) to other parts of the body. Approximately 20% of skin cancer develops from squamous cells and is called squamous cell carcinoma. This type of cancer is mainly caused by sun exposure, but it can appear on skin that has been burned, damaged by chemicals, or exposed to x-rays. Sites of a chronic inflammatory skin condition, mucous membranes (skin that lines the mouth, nose, anus, and a woman's vagina), and the lips are susceptible to squamous cell carcinoma. Squamous cell carcinoma rarely metastasizes, but it is more likely to spread than basal cell carcinoma. Methods of identifying non-melanoma skin cancers are known in the art. Generally, a skilled artisan may be able to diagnose a non-melanoma skin cancer via an examination. However, a biopsy may also be used to diagnose a non-melanoma skin cancer.

In still yet another aspect, the invention encompasses a method of treating melanoma skin cancer. The method comprises identifying a patient with melanoma skin cancer and topically administering to the melanoma skin cancer a composition comprising a cytotoxic agent and a TSLP inducer, wherein the melanoma skin cancer is reduced in size. In a specific embodiment, the composition may be administered for up to 10 days. Melanoma occurs when cancer cells form in skin cells called melanocytes. Specifically, methods of the invention may be used to treat melanoma in situ (MIS). MIS is also referred to as Stage 0 melanoma. In Stage 0, abnormal melanocytes are found in the epidermis. Generally, MIS affects only the top layer of the skin. These abnormal melanocytes may become cancer and spread into nearby normal tissue. Methods of diagnosing and identifying melanoma are known in the art. Generally, melanoma may be diagnosed based on family history, patient history, clinical presentation, and/or a skin exam biopsy of a mole that has changed size, shape or color, has irregular borders or edges, is more than one color, is asymmetrical, itches, or oozes, bleeds or is ulcerated, a change in pigmented skin or satellite moles.

Administration of a composition of the invention may result in greater than 50% reduction in lesion size relative to standard of care. For example, administration of a composition of the invention may result in greater than 55%, greater than 60%, greater than 65%, greater than 70%, greater than 75%, greater than 80%, greater than 85%, greater than 90%, greater than 95%, or 100% reduction in lesion size relative to standard of care. For example, a composition comprising 5-FU and a vitamin D analog may result in greater than 50% reduction in lesion size relative to a composition comprising 5-FU as the sole active agent. In some embodiments, administration of a composition comprising 5-FU and a vitamin D analog may result in greater than 55%, greater than 60%, greater than 65%, greater than 70%, greater than 75%, greater than 80%, greater than 85%, greater than 90%, greater than 95%, or 100% reduction in lesion size relative to a composition comprising 5-FU as the sole active agent. In an embodiment where a 100% reduction in lesion size has occurred, it may be deemed that the lesion has been cleared.

Methods of the invention may decrease the incidence and/or severity of adverse events relative to the incidence and/or severity of adverse events common during the standard of care treatment. Non-limiting examples of adverse events during topical use of a cytotoxic agent include: local pain, pruritus, itchiness, burning, stinging, crusting, weeping, dermatitis, photosensitivity, headache, insomnia, irritability, rash, leukocytosis, thrombocytopenia, birth defects, inflammation, miscarriage, Herpes simplex, allergic contact dermatitis, telangectasia, hyper- or hypopigmentation and scarring. Specifically, the incidence and/or severity of redness, scaling, crusting, itching and burning may be decreased relative to the standard of care treatment. For example, there may be a 30%, 35%, 40%, 45%, 50%, 55%, 60%, 65%, 70%, 75%, 80%, 85%, 90%, 95% or 100% decrease in the incidence and/or severity of adverse events relative to the standard of care treatment.

(a) Administration

In certain aspects, a therapeutically effective amount of a composition of the invention may be administered to a subject. Administration is performed using standard effective techniques. In a preferred embodiment, a composition is administered topically. A composition of the invention may be administered topically as an ointment, cream, suspension, lotion, powder, solution, paste, gel, spray, aerosol, salve, patch or oil. In some embodiments, a composition of the invention is administered as a topical ointment or cream.

For therapeutic applications, a therapeutically effective amount of a composition of the invention is administered to a subject. A "therapeutically effective amount" is an amount of the therapeutic composition sufficient to produce a measurable response (e.g., reduction in lesion size, reduction in number of lesions, reduction in toxicity and improved tolerability of treatment, induction of TSLP, reduction in symptoms associated with lesions such as redness, scaling, crusting, itching, burning, and thickness, normalization of keratinocyte differentiation and gene expression, restoration of epidermal integrity with competent barrier functions, reduction in aberrant cell proliferation and inflammation). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the precancerous lesion, the non-melanoma skin cancer, the melanoma skin cancer, the wart, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The timing of administration of the treatment relative to the disease itself and duration of treatment will be determined by the circumstances surrounding the case. Treatment could begin in a hospital or clinic itself, or at a later time after discharge from the hospital or after being seen in an outpatient clinic.

In an aspect, administration of a composition of the invention may result in a shortened duration of treatment relative to the standard of care. For example, the standard of care may be twice daily for 2 weeks. However, applicants have unexpectedly discovered that a shortened duration of therapy results in a significant reduction in lesion size relative to the standard of care. Accordingly, the duration of treatment may be less than 14 days. For example, the duration of treatment may be for about 13 days, about 12 days, about 10 days, about 9 days, about 8 days, about 7 days, about 6 days, about 5 days, about 4 days, about 3 days, about 2 days or about 1 day. In certain embodiments, the duration of treatment may be for 10 days, 7 days, 6 days, 5 days, 4 days, 3 days or 2 days. In an embodiment, the duration of treatment may be for up to 7 days. In another embodiment, the duration of treatment may be for between 4 to 6 days. In a specific embodiment, the duration of treatment may be for 4 days. In another specific embodiment, the duration of treatment may be for 6 days.

The standard of care frequency of dosing is twice daily. Accordingly, the frequency of dosing of a composition of the invention may be twice daily. Alternatively, it is contemplated that the frequency of dosing may be altered. For example, the frequency of dosing may be once, twice or three times daily. An increase in the frequency of dosing may result in a decreased duration of treatment. Alternatively, a decrease in the frequency of dosing may result in an increased duration treatment.

(b) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

The human subject may be of any age. However, since melanoma, non-melanoma skin cancer and precancerous skin lesions are generally associated with aging, a human subject may be an older human subject. In some embodiments, the human subject may be about 20, 25, 30, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

Still further, the subject may be a subject at risk of developing a precancerous skin lesion. A skilled artisan would be able to determine a subject at risk of developing a precancerous skin lesion. For example, a subject may be determined to be at risk of developing a precancerous skin lesion based on family history, patient history, clinical presentation, a skin exam biopsy, a dermascopy, sun exposure, and/or skin exposure to chemicals or x-rays. Specific areas at risk may include sun-exposed areas such as the face, bald scalp, lips, and the back of the hands.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Clinical Trial to Assess the Role of Calcipotriol in Treatment of Precancerous Skin Lesions Objectives:

The inventors hypothesized that calcipotriol can be used to create an antitumor immune environment in the human skin leading to elimination of actinic keratoses. Accordingly, the inventors conducted a clinical trial to examine this hypothesis. The aim of the clinical trial was to determine the therapeutic potential of calcipotriol in treatment of actinic keratoses in humans. Calcipotriol exerts its antitumor effects, at least in part, by modulating the immune environment in the skin. Therefore, in order to optimize the antigenic exposure of the immune cells attacking the skin tumors, calcipotriol's ability to augment the effects of a topical chemotherapeutic agent, 5-fluorouracil, that is currently used in clinic for treatment of actinic keratosis will be investigated. 5-fluorouracil induction of apoptosis in tumor cells will release antigens that can augment the immune response mounted by calcipotriol. Therefore, the response of patients with multiple actinic keratoses to topical calcipotriol+5-fluorouracil versus 5-fluorouracil alone over a 4-day twice daily treatment period will be compared. Treatment groups will be divided based on anatomical site of actinic keratosis lesions (scalp, face, right upper extremity and left upper extremity) in order to further delineate the site-specific effects of the treatments. The primary endpoint of the study is to compare the efficacy of topical 5-fluorouracil+calcipotriol vs. 5-fluorouracil alone in treatment of actinic keratosis in patients with multiple actinic keratoses at each of the four anatomical sites (scalp, face, right upper extremity and left upper extremity). The outcome of interest is percentage change from baseline number of actinic keratoses in the target treatment area on scalp, face, right upper extremity and left upper extremity at 8 weeks after treatment. Secondary endpoints of the study include: determining complete and partial (>75%) clearance of actinic keratoses at 8 weeks after treatment; determining the toxicity and tolerability of topical 5-fluorouracil+calcipotriol vs. 5-fluorouracil alone in treatment actinic keratosis at the end of 4-day treatment of course; examining the induction of TSLP expression in keratinocytes by calcipotriol at the site of the actinic keratoses at the end of 4-day treatment of course; determining any differences in response to topical 5-fluorouracil+calcipotriol vs. 5-fluorouracil alone between the four anatomical sites at 8 weeks after treatment.

Eligibility Criteria:

In this randomized double-blind clinical trial, participants with actinic keratoses were randomly assigned to receive 5-FU+calcipotriol (test group) or 5-FU+vaseline (control group) topical preparation for a twice-daily 4-day self-application.

TABLE 1

| Eligibility criteria—inclusion and exclusion | |
|---|---|
| Inclusion criteria | Exclusion criteria: |
| Age of at least 50 years | Treatment area is within 5 cm of an |
| Presence of four to fifteen clinically typical, visible, and discrete actinic keratoses in 25 cm2 on any of the four anatomical sites: scalp, face, right upper extremity and left upper extremity | incompletely healed wound or a suspected basal-cell or squamous-cell carcinoma Treatment area contained hypertrophic and hyperkeratotic lesions, cutaneous horns, or lesions that had not responded to repeated cryotherapy |
| Ability and willingness of the patient to participate in the study (Informed consent is obtained) | Recent (within a month) use of medications that could interfere with evaluation of the treatment area (e.g., topical medications, artificial tanners, immunosuppressive medications, immunomodulating agents, cytotoxic drugs, ultraviolet B phototherapy, other therapies for actinic keratoses, or oral retinoids) |
| | Premenopausal Women (to avoid any risk of pregnancy) |
| | History of hypercalcemia or clinical evidence of vitamin D toxicity |

Registration Procedure:

In this randomized double-blind study, 132 patients with actinic keratoses were recruited as they presented to Washington University dermatology clinics. The Dermatology Clinical Trials Unit at WUSM is nationally known for developing and participating in clinical therapeutic trials. The Clinical Trials Unit draws from the Division's large patient base—over 50,000 patient visits per year. Up to 15% of these visits are for the treatment of actinic keratosis [11]. >50-year-old patients that met the eligibility criteria for the study offered to participate in the study according to the IRB guidelines. If willing and able to participate, the patient was consented and registered into the study based on their anatomical site of treatment. If the participant has two or more qualified anatomical sites, one was picked as the primary anatomical site by the treating physician and the other sites were considered secondary sites. The primary anatomical site assignment was prioritized as Scalp>Face>Left upper extremity>Right upper extremity. In all cases, participants received one medication, which they applied to all of their affected sites in order to avoid any confusion. Four randomized list of medication were used, one for each primary anatomical site (scalp, face, right upper extremity and left upper extremity).

Treating physician chose the primary and secondary anatomical sites (if applicable) for treatment, documented the quantity of the clinically visible actinic keratoses, marked the lesions on transparencies and photographed the treatment area(s) separately. Participants were randomly assigned to receive 5-FU+calcipotriol (test group) or 5-FU+vaseline (control group) topical preparations by referring to the randomization list for their primary anatomical site. If the randomization list for an anatomical site was full (40 for each site), physician picked another qualified anatomical site as the primary site if present. Participants applied the study medication to all their qualified treatment area(s) twice daily for 4 consecutive days, starting the day after their first visit. Topical preparations were given to the participants at no cost at the initial visit. Participants were asked to return for follow-up visit on day 5 (i.e. the day after the last application), week 2 and 4 (both were recommended but not required) and week 8. On every follow-up visits, the treated skin was evaluated for any sign of irritation (including erythema, crusting or ulceration (using an erythema scale, Table 2)) and actinic keratoses were quantified clinically and photographed. They had their remaining actinic keratoses marked on transparencies at the last visits (8 week). Any participants that chose not to attend the week 2 and/or 4 visits was contacted by phone at week 2 and 4 time points, asked about the condition of their treated skin, presence of any adverse events, proper healing of the biopsy sites and asked to send photographs by email (if they agreed to email communication). All the records were kept in a locked office or password-protected computer that is only accessible by the members of the research team.

TABLE 2

Erythema scale allows quantification of the adverse skin effects associated with using the study medications

| | |
|---|---|
| 0 | No erythema |
| 1 | Mild erythema |
| 2 | Severe erythema with minimal scaling |
| 3 | Severe erythema with significant scaling |
| 4 | Severe erythema with scaling, crusting, itching and burning |

Figure 1B:
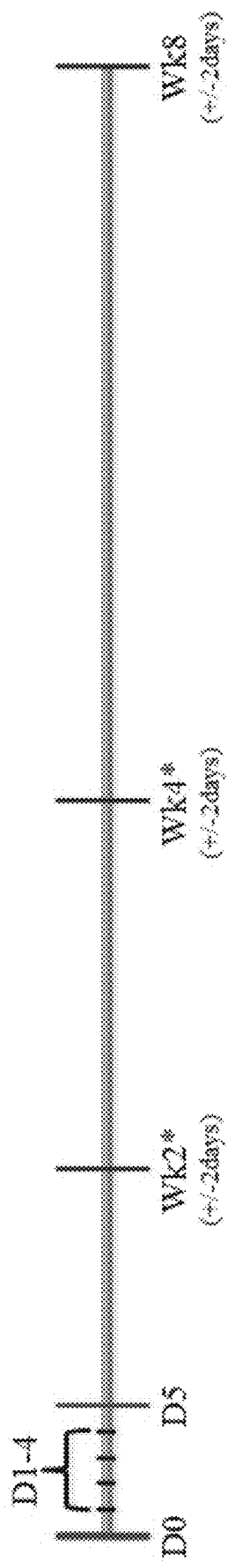
FIG. 1B depicts a diagram outlining the timeline for the clinical trial. Note that week 2 and 4 visits are optional. *: Weeks 2 and 4 visits are recommended but not required.

Research/Treatment Procedure:

At initial visit (Day 0), qualified actinic keratosis treatment area(s) were outlined, the lesions counted, marked on transparencies, photographed and study medication was assigned based on the randomization list corresponding to the participant's primary anatomical site (FIG. 1). Participants applied their assigned medication to all of their qualified anatomical sites, starting the day after their first visit. They were instructed to apply a thin layer of the medication to the affected skin to cover the whole area with their hand and thoroughly rub it into their skin twice a day (in morning and at bedtime) for four consecutive days. Participants were to wash their hands thoroughly after each application. Participants were to avoid exposure to either natural or artificial sunlight (including tanning booths, sun lamps, etc.) during the 4-day treatment period and use SPF 50+ sunscreen each day after applying the medication in the morning (sunscreen was provided to the participants). Participants were given a diary to document the time and date of their treatments, sunscreen use and record any side effects. Participants returned to clinic for reevaluation at day 5, week 2 (optional), 4 (optional) and 8. Participants' actinic keratosis count were determined clinically by the treating physicians and photographed at every visit. They had their remaining actinic keratoses marked on transparencies at the last (Week 8) visit. They were also evaluated for erythema and irritation using a standard erythema scale (Table 2; [12]). Participants that did not attend the week 2 and/or 4 visits were contacted by phone at those time points to determine the condition of their treated skin, biopsy sites and the presence of any adverse events. They were asked to send photographs of their treated skin by email (if they agreed to email communication). The primary end point for the study is the percent reduction from baseline in the total number of actinic keratoses at 8 weeks at each anatomical site. To confirm the induction of TSLP by calcipotriol treatment, we measured TSLP expression in 4 mm punch biopsies of the actinic keratosis before and after treatment. Treating physicians collected and labeled these skin samples based on the participants unique three digit ID (e.g. "201") without compromising their blinded status. We have processed the tissues for histological analysis using standard methods.

Medication preparation and storage: 5-fluorouracil 5% topical cream (Efudex; Taro Pharmaceuticals U.S.A. Inc., Hawthorne, N.Y.) was mixed with calcipotriol 0.005% topical ointment (calcitrene, calcipotriene, Dovonex; Taro Pharmaceuticals; test group) or vaseline (control group) at 1:1 weight ratio. The mixing of the two medications was performed at Division of Dermatology facility in accordance with USP 795 guidelines for non-sterile compounding conditions and under the supervision of Sitemann Cancer Center Investigational Drug Pharmacy. Also, the product labeling was in accordance with MO law requirements. 5-FU+calcipotriol and 5-FU+vaseline containers were labeled with a unique three-digit code (e.g. "201").

Each individual study medication container will also be labeled with the following general information: Participant's study ID number; The phrase, "For topical use only"; The phrase, "Store at controlled room temperature 15-25° C. (59-77° F.)"; The phrase, "CAUTION: New Drug—Limited to Investigational Use Only; Not for ophthalmic or intravaginal use"; and The phrase, "Keep out of reach of children". Medications will be stored in a locked cabinet at controlled room temperature (15-25° C.) at Washington University dermatology clinics site. Treating physicians will be blinded to the content of the containers (labeled with a unique three-digit code).

For product development purposes, the concentration of calcipotriol in the combination cream can be increased to achieve higher anti-tumor immune response but the concentration of 5-FU present in the current formulation (5%) is optimal based on our experimental data.

Skin biopsy: Before treatment (at first visit), one actinic keratosis lesion on face, scalp or upper extremity was biopsied by 4 mm punch biopsy procedure. After the 4-day treatment period (at day 5 visit), a treated actinic keratosis on face, scalp or upper extremity was biopsied by 4 mm punch biopsy procedure in order to determine the induction of gene and protein expression by calcipotriol application. A 4 mm punch biopsy tool was used to remove the skin and two absorbable sutures were placed to close the skin wound. Participants were instructed to avoid the "day 0" biopsy site during the 4-day treatment period. Skin samples were divided in half. One half was used for RNA preparation and the other froze in OCT medium or fixed in formaldehyde medium labeled only with study ID number and kept at −80° C. in a locked freezer or locked office until future processing for regular H&E staining and immunohistochemical analyses [13]. Participants received verbal and written wound care instruction. Participants were seen back in 5-10 days from the time of the procedure (Day 5 visit for the first biopsy; week 2 visit for the other two, recommended for these patients) to ensure complete healing of the wound, and treatment of any possible complications.

Lesion assessment: All actinic keratoses lesions were assessed and counted by clinical examination. The clinical diagnostic criteria included thick, scaly, or crusty pink papules in sun exposed areas. The diagnosis and counts were documented by photography at each visit and marked on transparencies at the first (Day 0) and the last (Week 8) visits.

Results:

Participant Demographics.

Figure 2:
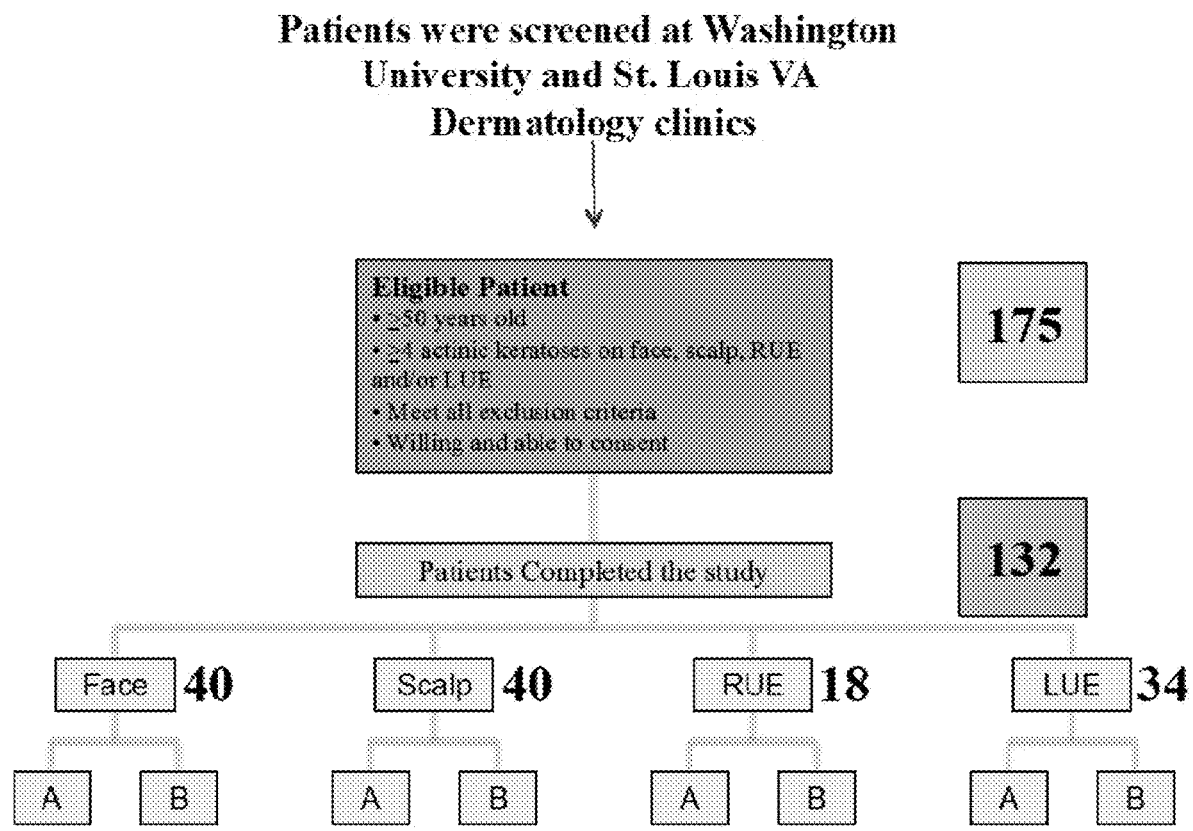
FIG. 2 depicts the patient demographics for the study. The number of eligible patients (175), the number that entered and completed the study (132) and their distribution based on their primary anatomical site is shown.

The number of eligible patients was 175, the number that entered and completed the study was 132 and their distribution based on their primary anatomical site is shown in FIG. 2. The age, gender and the amount of drug used (gram) per anatomical site treated are shown in Table 3. There is no significant difference between the test and the control group with regard to any of the parameters listed.

TABLE 3

Participant demographics.

|  |  | 5-FU + Calcipotriol | 5-FU + Vaseline |
|---|---|---|---|
| Age (mean ± SD) |  | 69 ± 7 | 70 ± 9 |
| Gender | # Male | 52 | 55 |
|  | # Female | 13 | 12 |
| Drug amount used (gram per anatomical site) |  | 7.015 | 7.7224 |

Percent Reduction in Number of Actinic Keratosis at Each Anatomical Site.

Figure 3:
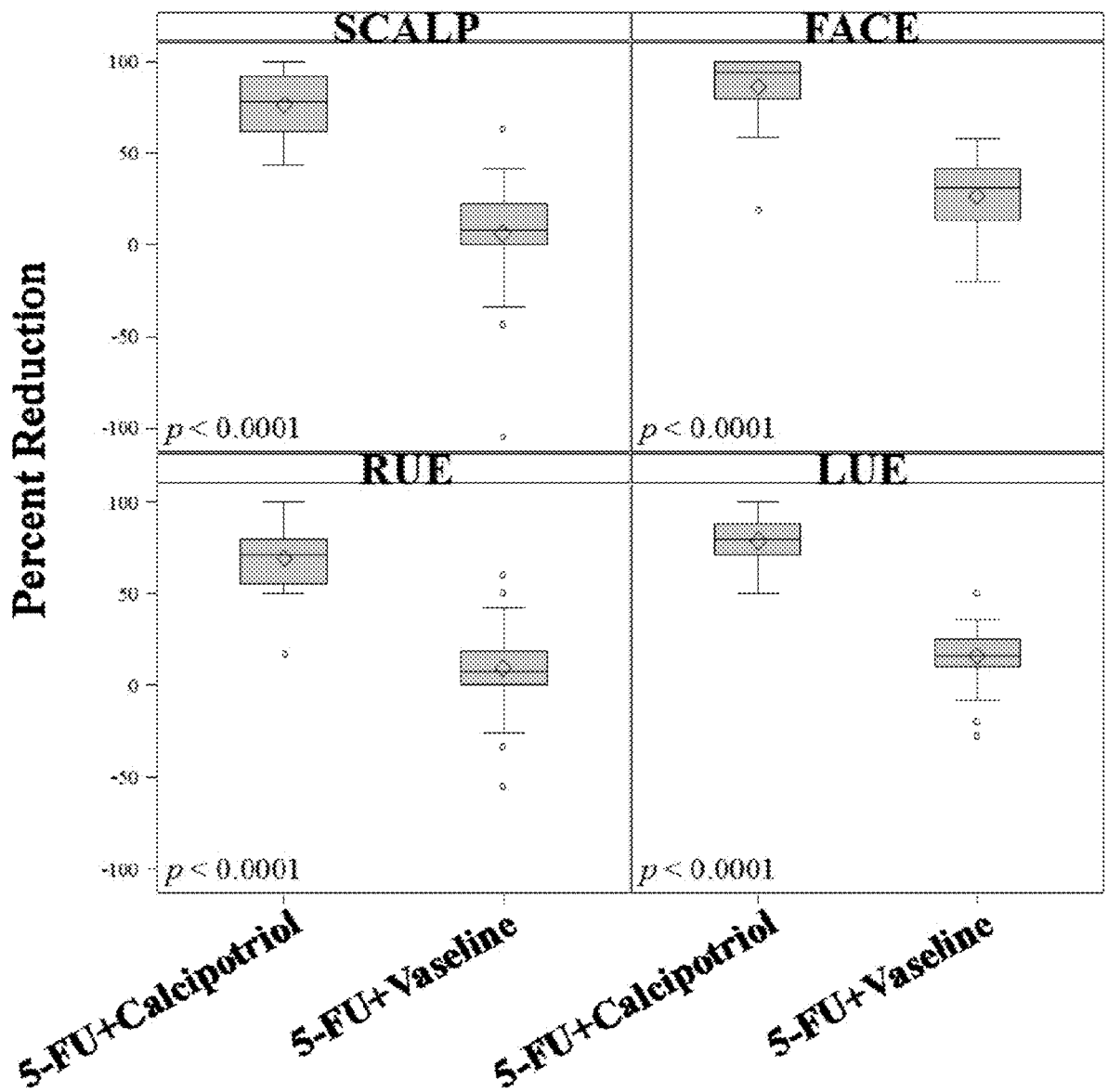
FIG. 3 depicts the percent reduction in actinic keratosis lesions between calcipotriol+5-fluorouracil and 5-fluorouracil treatments. Four days twice-daily treatment with 5-FU+calcipotriol combination results in significantly higher clearance of actinic keratoses (AKs) compared to standard of care treatment (5-FU+vaseline) at 8 weeks follow-up (p<0.0001 for all anatomical sites, Student's t-test; RUE: right upper extremity; LUE: left upper extremity).

Four days twice-daily treatment with 5-FU+calcipotriol combination results in significantly higher clearance of actinic keratoses (AKs) compared to standard of care treatment (5-FU+vaseline) at 8 weeks follow-up ($p<0.0001$ for all anatomical sites, Student's t-test; RUE: right upper extremity; LUE: left upper extremity) (FIG. 3). The detailed statistical analyses are shown in Table 4.

TABLE 4

Percent reduction in lesion size between calcipotriol + 5-fluorouracil and 5-fluorouracil treatments

|  | Drug | N | Mean | Std Dev | Std Err | Minimum | Maximum |
|---|---|---|---|---|---|---|---|
| Scalp | A (calcipotriol + 5-FU) | 34 | 76.4464 | 16.9467 | 2.9063 | 42.8571 | 100.0 |
|  | B (5-FU) | 34 | 5.6929 | 28.5432 | 4.8951 | −104.8 | 62.9630 |
|  | Diff (1 − 2) |  | 70.7535 | 23.4724 | 5.6929 | P value | <0.0001 |
| Face | A (calcipotriol + 5-FU) | 46 | 86.3334 | 16.4084 | 2.4193 | 18.7500 | 100.00 |
|  | B (5-FU) | 50 | 26.3526 | 20.8585 | 2.9498 | −21.0526 | 57.1429 |
|  | Diff (1 − 2) |  | 59.9808 | 18.8596 | 3.8530 | P value | <0.0001 |
| RUE | A (calcipotriol + 5-FU) | 23 | 69.1583 | 17.9170 | 3.7360 | 16.6667 | 100.0 |
|  | B (5-FU) | 25 | 9.5808 | 24.9161 | 4.9832 | −54.5455 | 60.0000 |
|  | Diff (1 − 2) |  | 59.5775 | 21.8503 | 6.3131 | P value | <0.0001 |
| LUE | A (calcipotriol + 5-FU) | 32 | 79.0029 | 13.6012 | 2.4044 | 50.0000 | 100.0 |
|  | B (5-FU) | 30 | 15.8891 | 17.4973 | 3.1946 | −27.5862 | 50.0000 |
|  | Diff (1 − 2) |  | 63.1138 | 15.6063 | 3.9661 | P value | <0.0001 |

Adverse Events.

Figure 4:
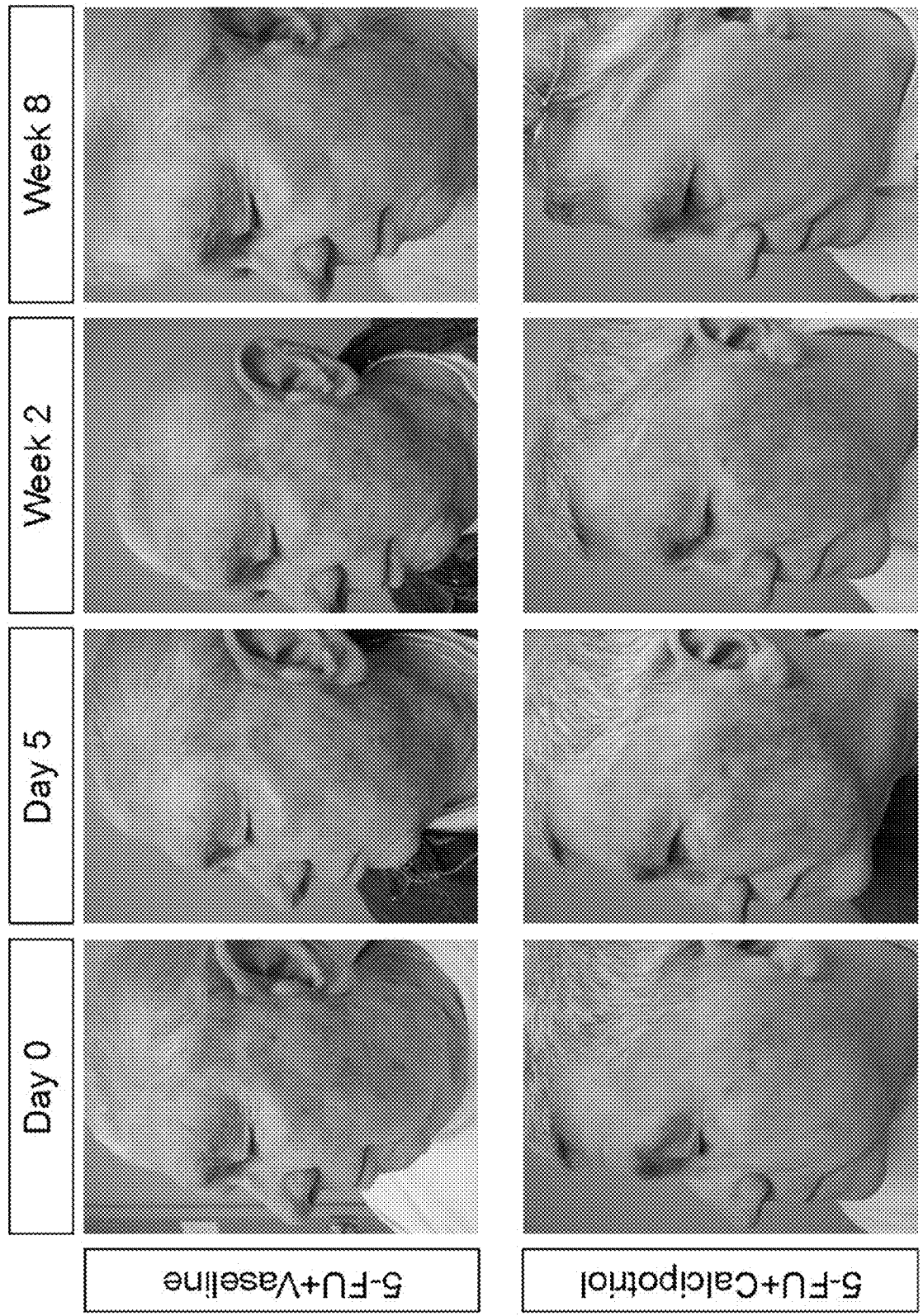
FIG. 4 depicts images of the adverse events associated with the treatment regiments. Participants treated with 5-FU+calcipotriol twice daily for 4 days developed marked inflammation centered around the sites of actinic keratoses as seen right after the last treatment (Day 5) and 10 days after the treatment is stopped (Week 2).
Figure 5A:
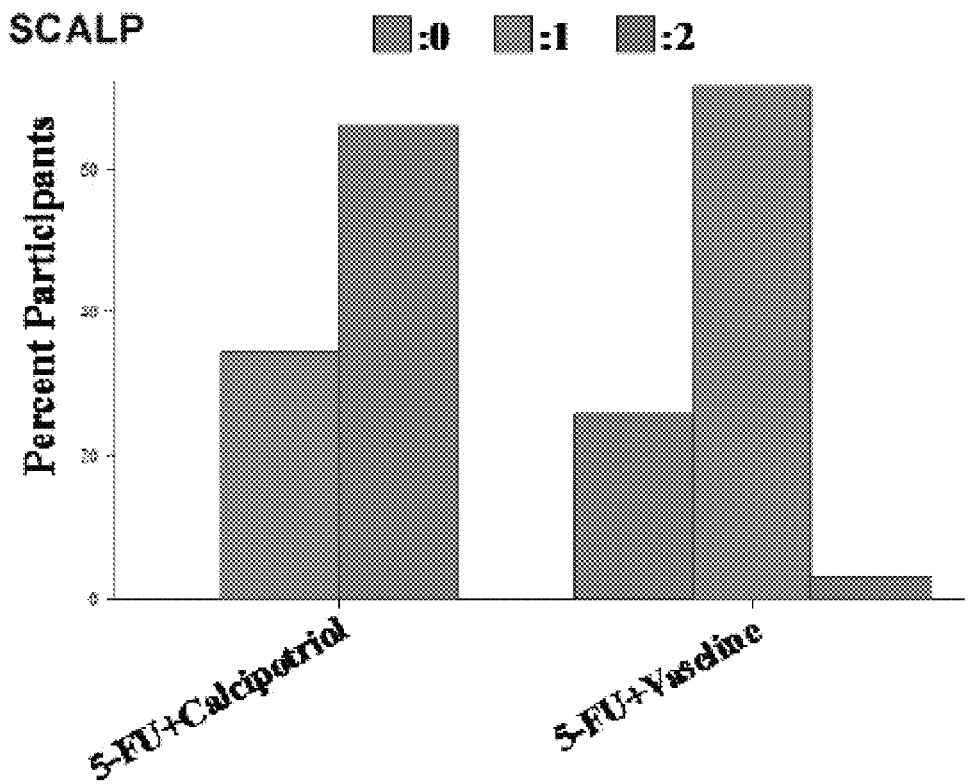
FIG. 5A, FIG. 5B, FIG. 5C and FIG. 5D depict graphs showing the percentage of participants with erythema scores of 0, 1 and 2 for each treated anatomical site.
Figure 5B:
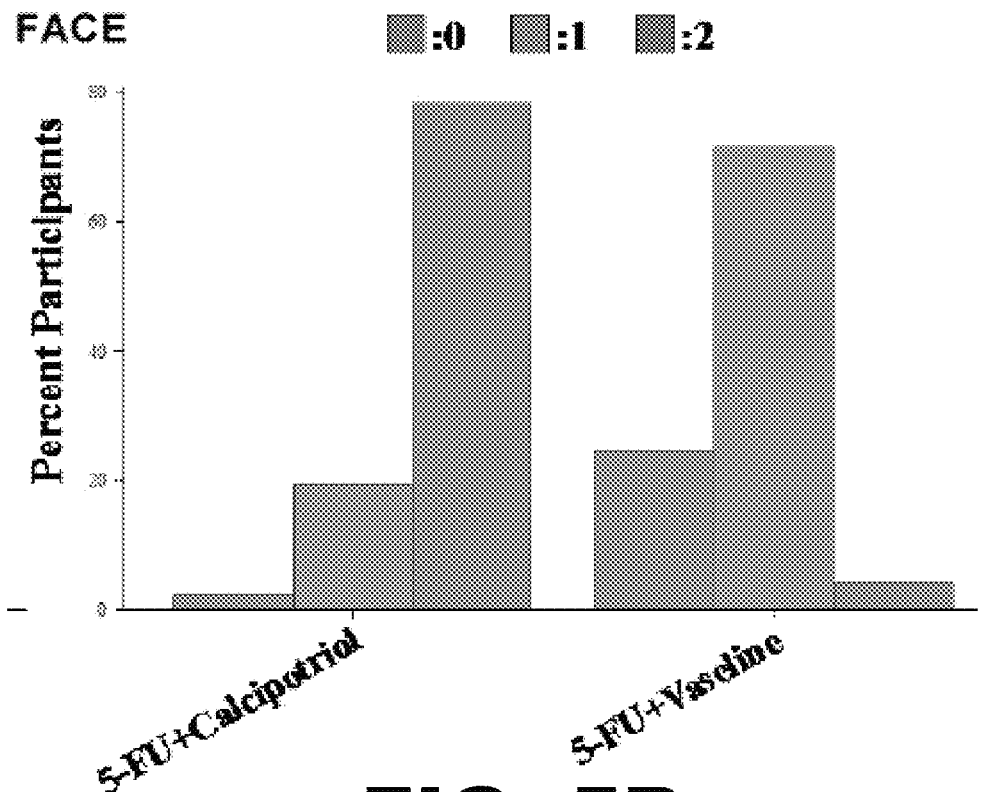
Figure 5C:
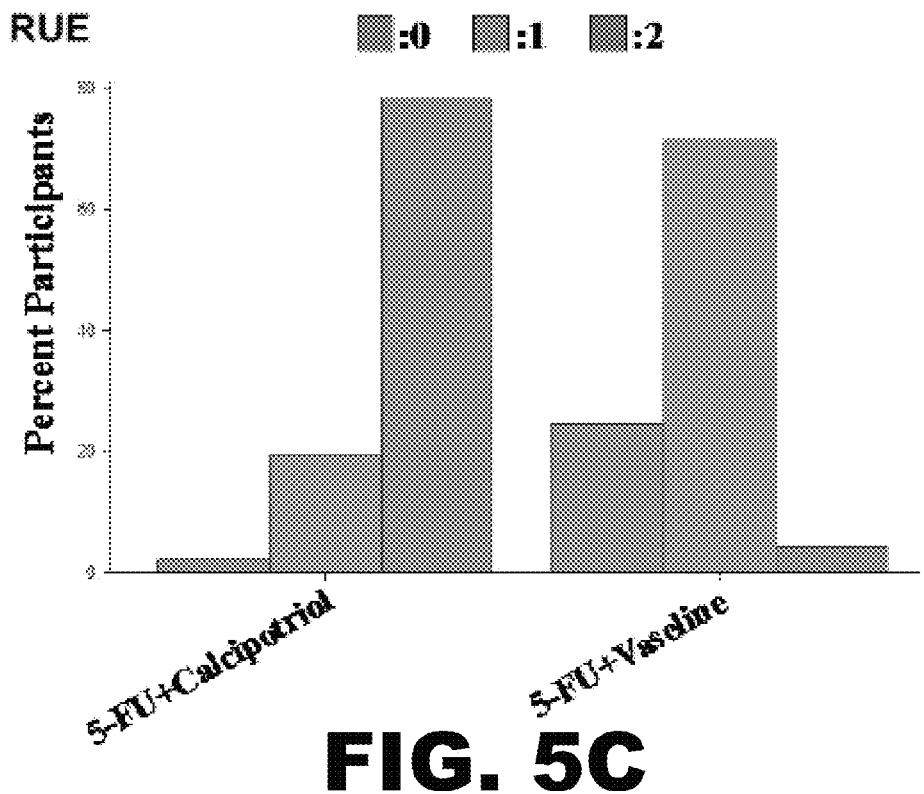
Figure 5D:
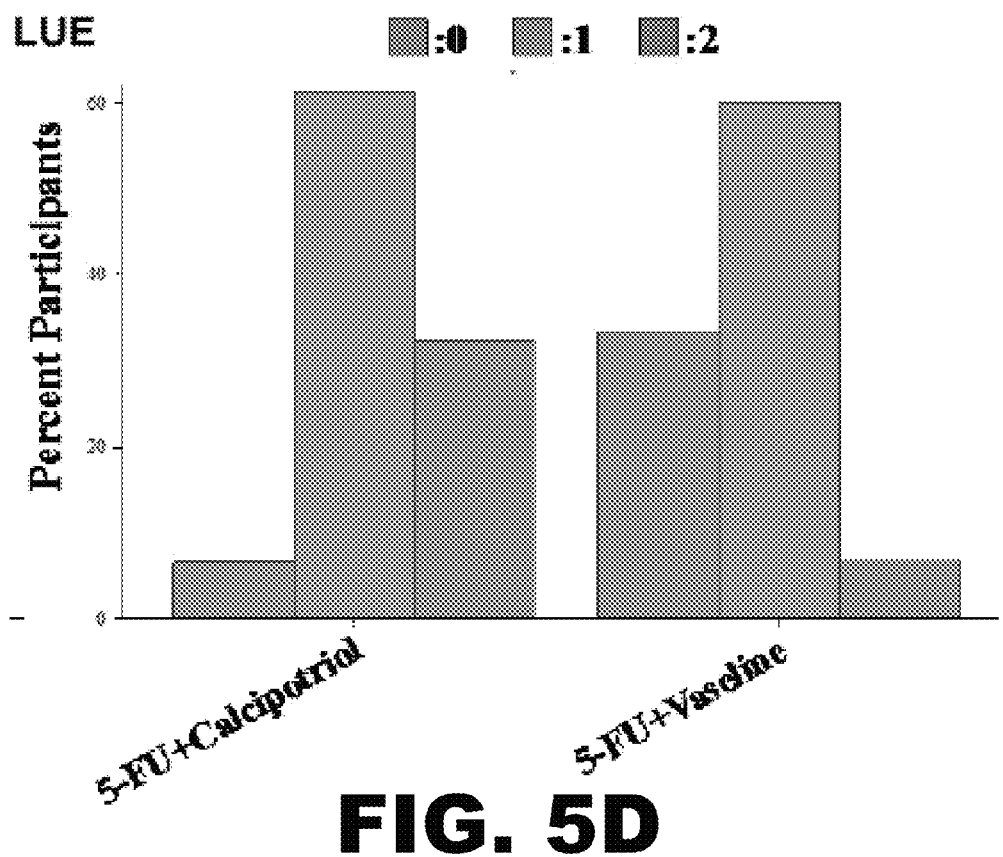

Erythema is the only adverse event observed in this study, which corresponds to the level of immune activation (i.e., inflammation) in the skin. Participants treated with 5-FU+calcipotriol twice daily for 4 days developed marked inflammation centered around the sites of actinic keratoses as seen right after the last treatment (Day 5) and 10 days after the treatment is stopped (Week 2) (FIG. 4). This inflammation is expected based on our hypothesis that calcipotriol induces immune system to attack the AKs in the skin. The percentage of participants with erythema scores of 0, 1 and 2 are shown for each treated anatomical site in FIG. 5. Note that due to short duration of the treatment, no participant experienced erythema scores of 3 or 4, which are commonly seen in patients treated with 5-FU twice daily for 2-3 weeks (standard of care regimen).

Skin Sample Collected from the Site of Actinic Keratosis (AK) are Used to Determine the Mechanism of 5-FU+Calcipotriol Action Against AK.

Figure 6C:
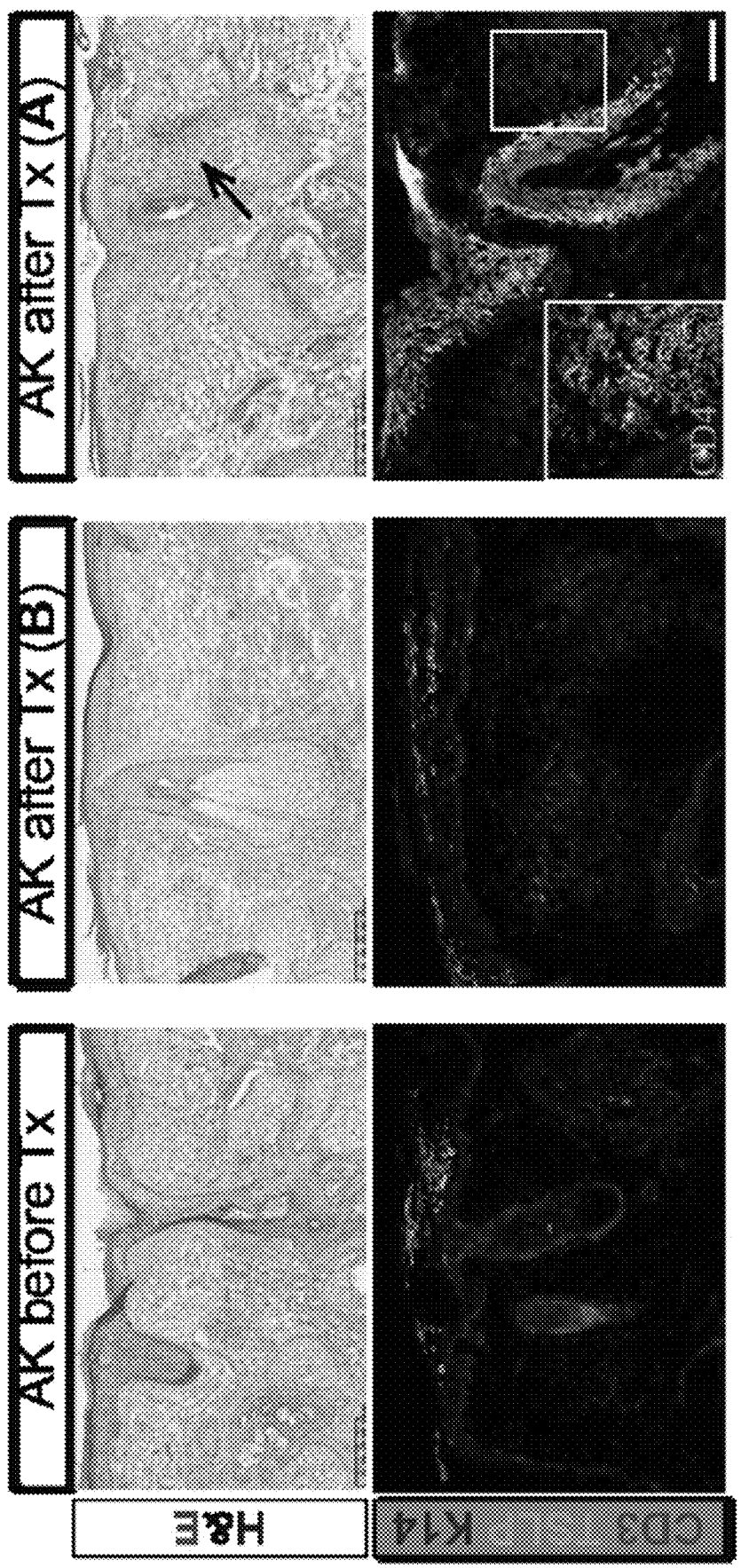
FIG. 6C depicts Hematoxylin and Eosin (H&E) stained sections from AKs before and after treatment. The images show the accumulation of lymphocytes in the upper dermis mainly in AK after treatment (Tx) in participant treated with 5-FU+Calcipotriol (arrow). The immunofluorescence staining of AKs before and after treatment also shows a robust TSLP expression in AK after treatment in participant treated with 5-FU+Calcipotriol including the accumulation of CD3+ T cells near dermal-epidermal junction. The majority of these T cells are CD4+T helper cells (inset). K14 marks the skin keratinocytes.

Hematoxylin and Eosin (H&E) stained sections from AKs before and after treatment are shown in FIG. 6. The images show the accumulation of lymphocytes in the upper dermis mainly in AK after treatment (Tx) in participant treated with 5-FU+Calcipotriol (arrow). The immunofluorescence staining of AKs before and after treatment also shows a robust TSLP expression in AK after treatment in participant treated with 5-FU+Calcipotriol including the accumulation of CD3+ T cells near dermal-epidermal junction. The majority of these T cells are CD4+T helper cells (inset). K14 marks the skin keratinocytes.

REFERENCES FOR THE EXAMPLE

1. Kim, R. H. and A. W. Armstrong, *Nonmelanoma skin cancer*. Dermatol Clin, 2012. 30(1): p. 125-39, ix.
2. Fenske, N. A., J. Spencer, and F. Adam, *Actinic keratoses: past, present and future*. J Drugs Dermatol, 2010. 9(5 Suppl ODAC Conf Pt 1): p. s45-9.
3. Warino, L., et al., *Frequency and cost of actinic keratosis treatment*. Dermatol Surg, 2006. 32(8): p. 1045-9.
4. Devaux, S., et al., *Topical vitamin D analogues alone or in association with topical steroids for psoriasis: a systematic review*. J Eur Acad Dermatol Venereol, 2012. 26 Suppl 3: p. 52-60.
5. Li, M., et al., *Topical vitamin D3 and low-calcemic analogs induce thymic stromal lymphopoietin in mouse keratinocytes and trigger an atopic dermatitis*. Proc Natl Acad Sci USA, 2006. 103(31): p. 11736-41.
6. Ziegler, S. F. and D. Artis, *Sensing the outside world: TSLP regulates barrier immunity*. Nat Immunol, 2010. 11(4): p. 289-293.
7. Demehri, S., et al., *Elevated epidermal thymic stromal lymphopoietin levels establish an antitumor environment in the skin*. Cancer Cell, 2012. 22(4): p. 494-505.
8. Di Piazza, M., et al., *Loss of Cutaneous TSLP-Dependent Immune Responses Skews the Balance of Inflammation from Tumor Protective to Tumor Promoting*. Cancer Cell, 2012. 22(4): p. 479-93.

9. Tanghetti, E. A., *The role of topical vitamin D modulators in psoriasis therapy*. J Drugs Dermatol, 2009. 8(8 Suppl): p. s4-8.
10. Lebwohl, M., et al., *Ingenol mebutate gel for actinic keratosis*. N Engl J Med, 2012. 366(11): p. 1010-9.
11. Davis, S. A., et al., *Top dermatologic conditions in patients of color: an analysis of nationally representative data*. J Drugs Dermatol, 2012. 11(4): p. 466-73.
12. Fullerton, A., et al., *Guidelines for measurement of skin colour and erythema. A report from the Standardization Group of the European Society of Contact Dermatitis*. Contact Dermatitis, 1996. 35(1): p. 1-10.
13. Soumelis, V., et al., *Human epithelial cells trigger dendritic cell mediated allergic inflammation by producing TSLP*. Nat Immunol, 2002. 3(7): p. 673-80.

What is claimed is:

1. A topical composition comprising about 2% to about 5% (wt/wt) 5-fluorouracil (5-FU) and about 0.002% to about 0.005% (wt/wt) calcipotriol.

2. The composition of claim 1, wherein the composition comprises from 3% to 5% (wt/wt) 5-fluorouracil (5-FU) and 0.003% to 0.005% (wt/wt) calcipotriol.

3. The composition of claim 1, wherein the composition further comprises at least one pharmaceutically acceptable excipient.

4. The composition of claim 3, wherein the composition is formulated as an ointment, cream, suspension, lotion, powder, solution, paste, gel, spray, aerosol, or oil.

5. The composition of claim 4, wherein the composition is formulated for transdermal or transmucosal administration.

6. The composition of claim 1, wherein the composition comprises one or more additional drugs or therapeutically active agents.

7. A method of treating a noncancerous skin lesion in a subject in need thereof, the method comprising, topically administering to the noncancerous skin lesion a composition comprising a cytotoxic agent and a thymic stromal lymphopoietin (TSLP) inducer.

8. The method of claim 7, wherein the TSLP inducer is calcipotriol.

9. The method of claim 7, wherein the cytotoxic agent is 5-fluorouracil (5-FU).

10. The method of claim 9, wherein the composition comprises about 2% to about 5% 5-FU.

11. The method of claim 10, wherein the composition comprises about 0.002% to about 0.005% calcipotriol.

12. The method of claim 7, wherein the noncancerous skin lesion is a wart or a similar virus infection of the skin.

13. The method of claim 12, wherein the wart is a plantar wart, cutaneous wart, ano-genital wart, verruca vulgaris, flat wart, filiform wart, or wart-like lesion associated with a virus infection of the skin.

14. A method of treating non-melanoma skin cancer in a subject in need thereof, the method comprising, topically administering to the non-melanoma skin cancer a composition comprising a cytotoxic agent and a thymic stromal lymphopoietin (TSLP) inducer.

15. The method of claim 14, wherein the TSLP inducer is calcipotriol.

16. The method of claim 14, wherein the cytotoxic agent is 5-fluorouracil (5-FU).

17. The method of claim 16, wherein the composition comprises about 2% to about 5% 5-FU.

18. The method of claim 17, wherein the composition comprises about 0.002% to about 0.005% calcipotriol.

19. The method of claim 14, wherein the non-melanoma skin cancer is a basal cell carcinoma, Bowen disease, kera-toacanthomas, Merkel cell carcinoma, cutaneous (skin) lymphomas, Kaposi sarcoma, skin adnexal tumors, sebaceous gland carcinoma, or sarcoma.

* * * * *